(12) United States Patent
Mochizuki et al.

(10) Patent No.: US 9,910,141 B2
(45) Date of Patent: Mar. 6, 2018

(54) ULTRASONIC DIAGNOSTIC APPARATUS, ULTRASONIC-DIAGNOSITC-APPARATUS MAIN BODY, AND ULTRASONIC PROBE

(71) Applicant: Toshiba Medical Systems Corporation, Otawara-shi (JP)

(72) Inventors: Fumio Mochizuki, Nasushiobara (JP); Gen Nagano, Nasushiobara (JP); Kazuhito Nakata, Otawara (JP); Kenichi Unayama, Otawara (JP); Takeshi Fukasawa, Nasushiobara (JP); Koji Kuroiwa, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 133 days.

(21) Appl. No.: 14/821,331

(22) Filed: Aug. 7, 2015

(65) Prior Publication Data

US 2015/0346331 A1    Dec. 3, 2015

Related U.S. Application Data

(63) Continuation of application No. PCT/JP2014/052761, filed on Feb. 6, 2014.

(30) Foreign Application Priority Data

Feb. 7, 2013    (JP) .................................. 2013-022073

(51) Int. Cl.
*G01S 7/00*    (2006.01)
*G01S 7/52*    (2006.01)
(Continued)

(52) U.S. Cl.
CPC ........ *G01S 7/52096* (2013.01); *A61B 8/4444* (2013.01); *A61B 8/56* (2013.01);
(Continued)

(58) Field of Classification Search
CPC ..... G10K 11/341; G01S 7/52096; A61B 8/56; A61B 8/444; A61B 8/4405
See application file for complete search history.

(56) References Cited

U.S. PATENT DOCUMENTS

| 2004/0158148 A1* | 8/2004 | Amemiya | ............. B06B 1/0215 |
| | | | 600/437 |
| 2005/0148878 A1* | 7/2005 | Phelps | .................... A61B 8/546 |
| | | | 600/459 |
| 2012/0200196 A1* | 8/2012 | Amemiya | ............. B06B 1/0207 |
| | | | 310/317 |

FOREIGN PATENT DOCUMENTS

| JP | 9-527 A | 1/1997 |
| JP | 09-000527 A | 1/1997 |

(Continued)

OTHER PUBLICATIONS

Combined Chinese Office Action and Search Report dated Jul. 6, 2016 in Patent Application No. 201480005923.4 (with English language translation of categories of cited documents).
(Continued)

*Primary Examiner* — Hovhannes Baghdasaryan
(74) *Attorney, Agent, or Firm* — Oblon, McClelland, Maier & Neustadt, L.L.P.

(57) ABSTRACT

According to on embodiment, a power supply circuit is provided in a main body and generates operating voltages for various electric circuits in the ultrasonic probe. Signal lines SL1 connects the power supply circuit to the electric circuits by way of the probe connector, to supply operating voltages from the power supply circuit to the electric circuits. A voltage monitoring circuit is provided in the main body and monitors voltages supplied to the electric circuits, utilizing the input voltage from the ultrasonic probe. To supply input voltages to the voltage monitoring circuit, signal line SL2 branches from signal lines SL1 in the
(Continued)

ultrasonic probe and connects the electric circuits and the voltage monitoring circuit to each other by way of the probe connector.

10 Claims, 5 Drawing Sheets

(51) Int. Cl.
  *A61B 8/00* (2006.01)
  *G10K 11/34* (2006.01)
(52) U.S. Cl.
  CPC ............ *G01S 7/5205* (2013.01); *A61B 8/4405* (2013.01); *G10K 11/341* (2013.01)

(56) References Cited

FOREIGN PATENT DOCUMENTS

| JP | 2003-135470 A | 5/2003 |
|----|---------------|--------|
| JP | 4176892 B2 | 11/2008 |
| JP | 41768292 B2 | 11/2008 |

OTHER PUBLICATIONS

International Search Report dated Apr. 15, 2014 for PCT/JP2014/052761 filed Feb. 6, 2014 with English Translation.
International Written Opinion dated Apr. 15, 2014 for PCT/JP2014/052761 filed Feb. 6, 2014.

\* cited by examiner

ULTRASONIC DIAGNOSTIC APPARATUS, ULTRASONIC-DIAGNOSITC-APPARATUS MAIN BODY, AND ULTRASONIC PROBE

CROSS-REFERENCE TO RELATED APPLICATIONS

This application is a Continuation Application of PCT Application No. PCT/JP2014/052761, filed Feb. 6, 2014 and based upon and claims the benefit of priority from the Japanese Patent Application No. 2013-022073, filed Feb. 7, 2013, the entire contents of all of which are incorporated herein by reference.

FIELD

Embodiments described herein relate to an ultrasonic diagnostic apparatus, an ultrasonic-diagnostic-apparatus main body, and ultrasonic probe.

BACKGROUND

An ultrasonic probe contains an ultrasonic transducer for transmitting and receiving ultrasonic waves. In one type of ultrasonic probe, ultrasonic transducers are connected, with a signal line, to a transmitting circuitry for transmitting a driving signal, and a high-voltage switch circuit is interposed. The switch circuit enables switching among the ultrasonic transducers, and the driving signal is supplied to the selected ultrasonic transducer. The high-voltage switch circuit operates on a high operating voltage applied from a power supply circuit of an ultrasonic-diagnostic-apparatus main body. If, for some reason or other, the driving signal is supplied without application of the operating voltage, the high-voltage switch circuit may be broken down. Therefore, the main body of an ultrasonic diagnostic apparatus to which an ultrasonic probe containing high-voltage switch circuit is connectable typically comprises a voltage monitoring circuit. The voltage monitoring circuit monitors the supply line of the operating voltage supplied from the power-supply circuit of the ultrasonic-diagnostic-apparatus main body to the high-voltage switch circuit. However, even if the signal line leading to the high-voltage switch circuit is not reliably connected to the probe connector, the operating voltage is kept supplied to the voltage monitoring circuit. For this reason, the voltage monitoring circuit provided in the ultrasonic-diagnostic-apparatus main body cannot sense an error.

Japanese Patent No. 4176892 discloses providing a voltage monitoring circuit for an ultrasonic probe. This type of ultrasonic diagnostic apparatus is featured in that a voltage monitoring circuit can sense an error even if the signal line leading to the high-voltage switch circuit is not reliably connected to the probe connector. However, the voltage monitoring circuit has to be provided for each of ultrasonic probes, and the cost of each ultrasonic probe and the cost of the ultrasonic diagnostic apparatus are inevitably high. This problem occurs not only where the operating voltage of a high-voltage switch circuit is monitored but also where the operating voltage of a device of an ultrasonic probe is monitored.

BRIEF DESCRIPTION OF THE DRAWING

FIG. 1 is a schematic diagram showing how an ultrasonic diagnostic apparatus of a first embodiment looks like.

DETAILED DESCRIPTION

In general, according to one embodiment, an ultrasonic diagnostic apparatus comprising (i) an ultrasonic probe including a head, a cable and a connection; and (ii) an ultrasonic-diagnostic-apparatus main body connected to the ultrasonic probe through the connector. the ultrasonic diagnostic apparatus includes an electric circuit, a first signal line, a power supply circuit, a second signal line, a third signal line, a voltage monitoring circuit, and a fourth signal line. The electric circuit is provided in the ultrasonic probe. The first signal line is passing through the cable and connected at one end to the electric circuit and at another end to the connector. The power supply circuit is provided in the main body and configured to generate an operating voltage of the electric circuit. The second signal line is provided inside the main body and connected at one end to the power supply circuit. The second signal line is connected at another end to the first signal line when the main body is connected to the ultrasonic probe. The third signal line is connected at one end to the first signal line and at another end to the connector. The voltage monitoring circuit is provided in the main body and configured to monitor a voltage supplied to the electric circuit, utilizing an input voltage. The fourth signal line is provided inside the main body and connected at one end to the voltage monitoring circuit, the fourth signal line being connected at another end to the third signal line when the main body is connected to the ultrasonic probe.

A description will now be given, with reference to the accompanying drawings, of an ultrasonic diagnostic apparatus, an ultrasonic-diagnostic-apparatus main body and ultrasonic probe according to embodiments.

First Embodiment

Figure 1:
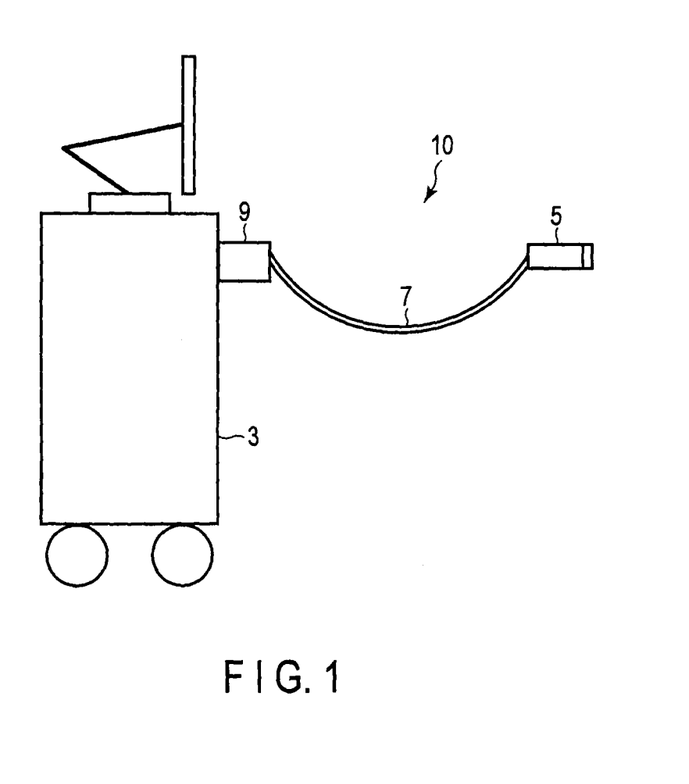

FIG. 1 is a schematic diagram showing how an ultrasonic diagnostic apparatus of a first embodiment looks like. As shown in FIG. 1, the ultrasonic diagnostic apparatus of the first embodiment comprises an ultrasonic probe 1 and an ultrasonic-diagnostic-apparatus main body 3. The ultrasonic probe 1 comprises a probe head 5, a probe cable 7 and a probe connector 9. The probe head 5 contains a plurality of devices 5. The probe cable 7 is connected at one end to the proximal portion of the probe head 5. The probe connector 9 is attached to the other end of the probe cable 7. The probe connector 9 is detachably connected to a slot (not shown) of the ultrasonic-diagnostic-apparatus main body 3. In the state where the probe connector 9 is connected to the ultrasonic-diagnostic-apparatus main body 3, various electric signals are transmitted and received between the ultrasonic probe 1 and the ultrasonic-diagnostic-apparatus main body 3.

Figure 2:
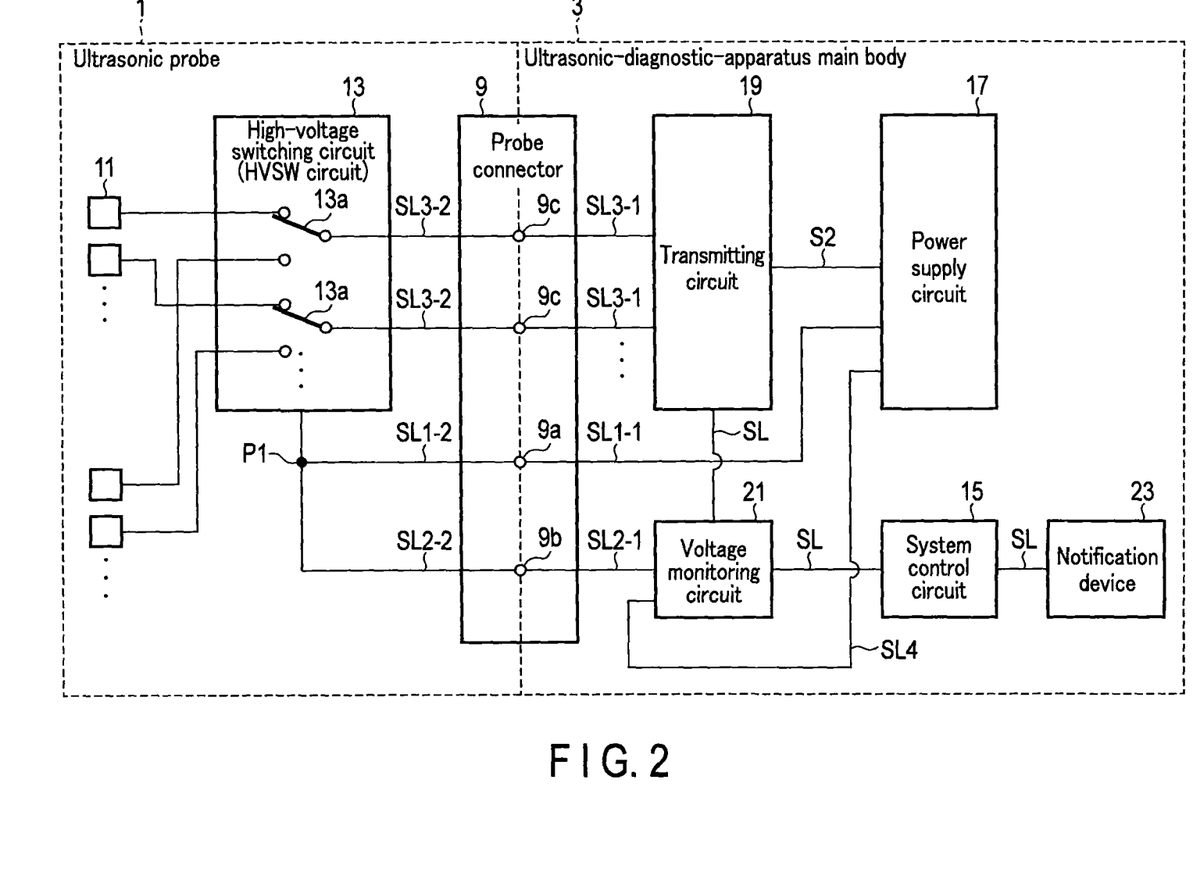
FIG. 2 is a diagram illustrating an ultrasonic probe and an ultrasonic-diagnostic-apparatus main body according to the first embodiment.

FIG. 2 is a diagram illustrating the ultrasonic probe 1 and the ultrasonic-diagnostic-apparatus main body 3 according to the first embodiment. In FIG. 2, a signal receiving circuit and the related system are not illustrated for simplicity.

As shown in FIG. 2, the ultrasonic probe 1 comprises a probe connector 9, a plurality of ultrasonic transducers 11, and a high-voltage switching circuit (hereinafter referred to as an HVSW circuit) 13. The ultrasonic-diagnostic-apparatus main body 3 comprises a system control circuitry 15 as a central element. It also comprises a power supply circuit 17, a transmitting circuitry 19, a voltage monitoring circuit 21 and a notification device 23.

The ultrasonic probe 1 is connected to the devices of the ultrasonic-diagnostic-apparatus main body 3 through signal lines SL. Of the signal lines, the signal line connecting the power supply circuit 17 and the HVSW circuit 13 will be referred to as an HVSW signal line SL1, the signal line connecting the HVSW 13 and the voltage monitoring circuit 21 will be referred to as a monitoring-voltage signal line SL2, and the signal lines connecting the transmitting circuitry 19 and the HVSW circuit 13 will be referred to as driving-signal-supply signal lines SL3. In the present embodiment, the signal lines are conductors permitting a current to flow therethrough. The electric signals flowing through the signal lines may be either analog signals or digital signals.

The HVSW signal line SL1 connects the power supply circuit 17 and the HVSW circuit 13 to each other by way of the probe connector 9. More specifically, the HVSW signal line SL1 includes: a first portion SL1-1 which connects the power supply circuit 17 and pin 9a of the probe connector 9 to each other inside the ultrasonic-diagnostic-apparatus main body 3; and a second portion SL1-2 which connects the HVSW circuit 13 and pin 9a of the probe connector 9 inside the ultrasonic probe 1.

The monitoring-voltage signal line SL2 branches from the HVSW signal line SL1 inside the ultrasonic probe 1 and connects the HVSW circuit 13 and the voltage monitoring circuit 21 to each other by way of the probe connector 9. More specifically, the monitoring-voltage signal line SL2 includes: a first portion SL2-1 which connects the power supply circuit 17 and pin 9b of the probe connector 9 to each other inside the ultrasonic-diagnostic-apparatus main body 3; and a second portion SL2-2 which connects the HVSW circuit 13 and pin 9b of the probe connector 9 inside the ultrasonic probe 1. Signal line SL1-2 is connected to signal line SL2-2 at branch point P1.

The driving-signal-supply signal lines SL3 connect the transmitting circuitry 19 and respective switches 13a of the HVSW circuit 13 to each other by way of the probe connector 9. More specifically, each driving-signal-supply signal line SL3 includes: a first portion SL3-1 which connects the power supply circuit 19 and pin 9c of the probe connector 9 to each other inside the ultrasonic-diagnostic-apparatus main body 3; and a second portion SL3-2 which connects the HVSW circuit 13 and pin 9c of the probe connector 9 inside the ultrasonic probe 3. For example, the number of driving-signal-supply signal lines SL3 is equal to the number of switches 13a of the HVSW circuit 13.

The power supply circuit 17 can generate a plurality of operating voltages to operate the ultrasonic probe 1 and the devices of the ultrasonic-diagnostic-apparatus main body 3. For example, the power supply circuit 17 generates an operating voltage required to operate the HVSW circuit 13 (the voltage will be hereinafter referred to as an HVSW operating voltage). The HVSW operating voltage is supplied to the HVSW circuit 13 through the HVSW signal line SL1. The power supply circuit 17 can also generate an operating voltage required to operate the transmitting circuitry 19. Furthermore, the power supply circuit 17 can generate not only the operating voltages but also a reference voltage to be supplied to the voltage monitoring circuit 21.

The transmitting circuitry 19 is applied with an operating voltage supplied through signal line SL from the power supply circuit 17, and operates on the operating voltage. The transmitting circuitry 19 generates a driving signal for driving the ultrasonic transducers 11 (the driving signal will be referred to as a transmission driving signal). More specifically, the transmitting circuitry 19 includes a trigger circuit, a delay circuit, a pulser circuit, etc., none of which are shown in the drawings. The pulser circuit repeatedly generates a rate pulse for formation of a transmitting ultrasonic wave at a predetermined rate frequency fr Hz (period: 1/fr seconds). The delay circuit provides a delay time determined in accordance with a transmitting direction and a transmitting focal position for each rate pulse according to channels. The trigger circuit applies a transmission driving signal to the ultrasonic transducers 11 at timings based on the rate pulse. Responsive to the application of the transmission driving signal, the ultrasonic transducers 11 transmit ultrasonic waves regarding the transmitting direction and transmitting focal position corresponding to the delay time.

The ultrasonic transducers 11 are housed in the distal end portion of the probe head 5. The ultrasonic transducers 11 are arranged in one dimension or in two dimensions. The ultrasonic transducers 11 receive a transmission driving signal supplied by way of the probe connector 9, and transmit an ultrasonic wave upon receipt of the transmission driving signal. The ultrasonic transducers 11 receive an ultrasonic wave reflected by an object to be examined, and transmit an echo signal upon receipt of the echo signal. The generated echo signal is supplied to the ultrasonic-diagnostic-apparatus main body through a signal line (not shown) and by way of the probe connector 9. Thereafter, the ultrasonic-diagnostic-apparatus main body 3 performs signal processing with respect to the echo signal, thereby generating an ultrasonic image. The generated ultrasonic image is displayed on a display provided for the ultrasonic-diagnostic-apparatus main body 3.

The high-voltage switch circuit (HVSW circuit) 13 operates on an HVSW operating voltage. The HVSW circuit 13 switches connections between the ultrasonic transducers 11 and the transmitting circuitry 19 so as to select an ultrasonic transducer 11 to which a transmission driving signal is to be supplied. The connection switching is performed by the HVSW circuit 13 each time an ultrasonic wave is transmitted and received. For example, the HVSW circuit 13 switches connections between the ultrasonic transducers 1 and the transmitting circuitry 19, in such a manner that the transmission opening is shifted by the distance corresponding to one ultrasonic transducer each time an ultrasonic wave is transmitted and received. Let us assume that the number of driving-signal-supply signal lines SL3 is N and the number of ultrasonic transducers 11 is M (M>N). To generate a first ultrasonic transmission beam, a transmission driving signal is supplied to the first to N-th ultrasonic transducers 11, and an ultrasonic wave is transmitted from the first to N-th ultrasonic transducers 11. To generate a next ultrasonic transmission beam, a transmission driving signal is supplied to the second to (N+1)th ultrasonic transducers 11, and an ultrasonic wave is transmitted from the second to (N+1)th ultrasonic transducers 11. In other words, connection switching is performed in such a manner that the transmission driving signal supplied to the first ultrasonic transducer 11 in the last ultrasonic wave transmission is supplied to the (N+1)th ultrasonic transducer 11. In this manner, the transmission opening is shifted in order. Even if the number of driving-signal-supply signal lines SL3 used for supplying a transmission driving signal to the ultrasonic transducers 11 is smaller than the number of ultrasonic transducers 11, ultrasonic scanning can be executed using all ultrasonic transducers 11.

Figure 3:
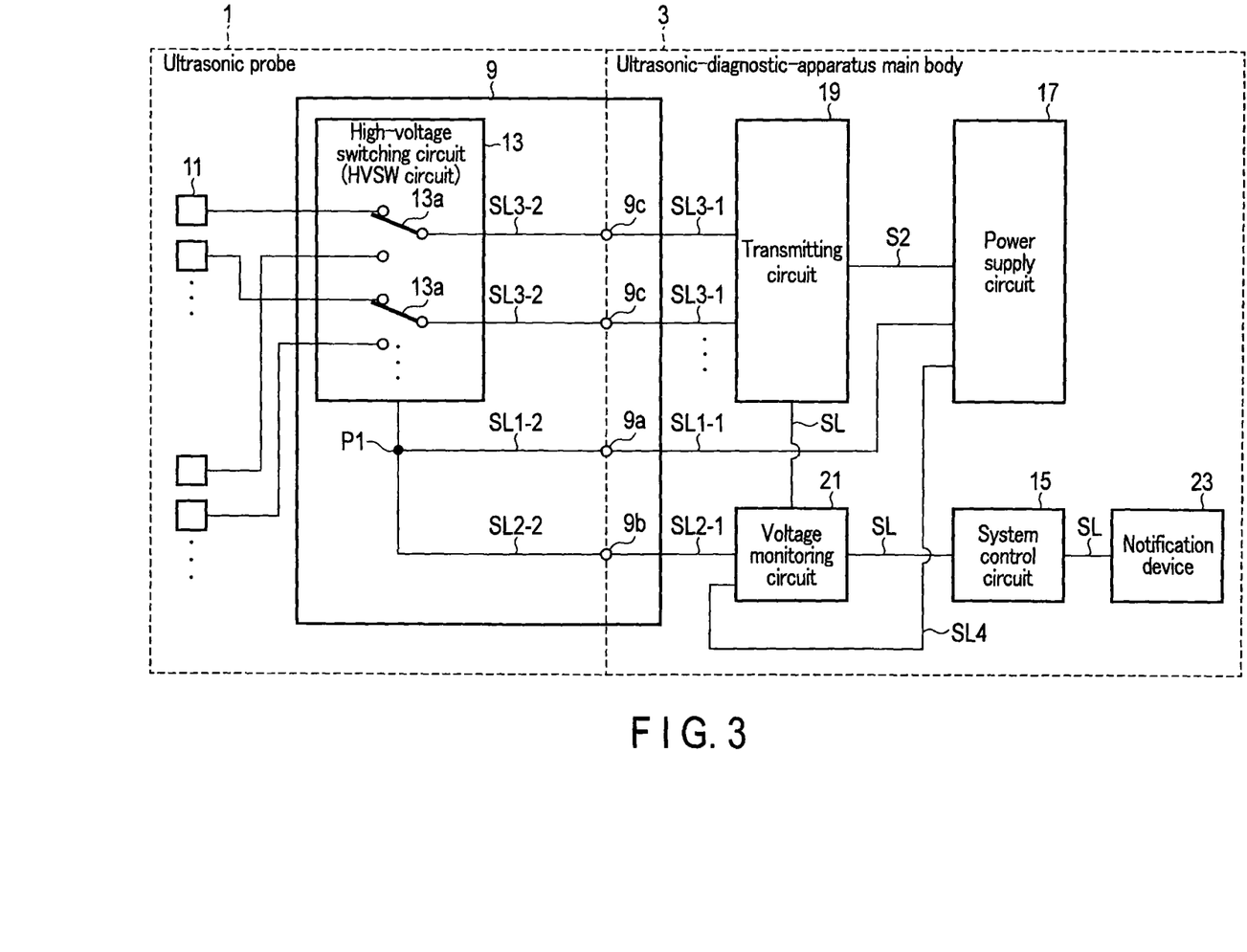
FIG. 3 is a diagram illustrating an ultrasonic probe and an ultrasonic-diagnostic-apparatus main body according to a modification of the first embodiment.

The HVSW circuit 13 may be incorporated in the probe head 5 of the ultrasonic probe 1 or in the probe connector 9. Where the HVSW circuit 13 is incorporated in the probe head 5, branch point P1 is provided in the probe header 5, on the probe cable 7 or in the probe connector 9. Where the HVSW circuit 13 is incorporated in the probe connector 9, branch point P1 is provided in the probe connector 9, as shown in FIG. 3.

The voltage monitoring circuit 21 receives a voltage from the monitoring voltage signal line SL2 as an input voltage. To be more specific, the voltage monitoring circuit 21 receives a voltage from signal line SL2 as an input signal, i.e., the signal line branching from the HVSW signal line SL1 (used for supplying an HVSW operating voltage) and extending from inside the ultrasonic probe 1 back to the ultrasonic-diagnostic-apparatus main body 3. The voltage monitoring circuit 21 monitors a voltage applied from the power supply circuit 17 to the HVSW circuit 13, utilizing the input voltage from the ultrasonic probe 1. Details of the voltage monitoring circuit 21 will be described later.

The notification device 23 makes a notification regarding the voltage supply state determined by the voltage monitoring circuit 21. For example, the notification device 23 makes a notification using a display, a speaker, a lamp, etc.

The system control circuitry 15 functions as a central element of the ultrasonic diagnostic apparatus of the present embodiment. To be specific, the system control circuitry 15 computes control data used by the devices and circuits of the ultrasonic probe 1 and ultrasonic-diagnostic-apparatus main body 3, in accordance with an ultrasonic scanning mode and scanning conditions which the user designates with an operation section (not shown). The computed control data are transmitted to the respective devices.

Incidentally, the notification device 23 and the system control circuitry 15 may be implemented by a single circuit or plurality of circuits. The single circuit or the plurality of circuits includes a processing unit such as CPU (central processing unit), MPU (micro processing unit), and GPU (graphical processing unit) and a storage unit such as HDD (hard disk drive), SSD (solid state drive), ROM (read only memory), and RAM (random access memory). The single circuit or the plurality of circuits executes the control function described above.

Next, a description will be given of an example of the operation performed by the ultrasonic diagnostic apparatus according to the first embodiment. As described above, the voltage monitoring circuit 21 receives a voltage from the monitoring voltage signal line SL2 as an input voltage. Where the power supply circuit 17 and the HVSW circuit 13 are connected in the normal manner, the operating voltage applied to the HVSW circuit 13 is an input voltage supplied to the voltage monitoring circuit 21. Where the power supply circuit 17 and the HVSW circuit are not connected in the normal manner, the operating voltage applied to the HVSW circuit 13 is not an input voltage supplied to the voltage monitoring circuit 21. The case where the power supply circuit 17 and the HVSW circuit are not in good contact is, for example, a case where the contact between the HVSW signal line SL1-2 of the ultrasonic probe 1 and the HVSW signal line SL1-1 of the ultrasonic-diagnostic-apparatus main body 3 is defective inside the probe connector 9.

To detect such a defective contact in the probe connector 9, the voltage monitoring circuit 21 determines whether the input voltage from the monitoring-voltage signal line SL2 is within an allowable range. If the input voltage is not determined to be within the allowable range, the voltage monitoring circuit 21 generates an electric signal to this effect (the electric signal will be referred as an error signal). If the input voltage is determined to be within the allowable range, the voltage monitoring circuit 21 does not generate an error signal. When the input voltage is determined to be within the allowable range, the voltage monitoring circuit 21 may generate an electric signal to this effect (the electric signal will be referred to as an allowance signal). The allowance signal and the error signal are supplied to the system control circuitry and the transmitting circuitry 19 through signal line SL. In the description below, the voltage monitoring circuit 21 will mentioned, referring to the case where neither the error signal nor the allowance signal is generated if the input voltage is determined to be within the allowable range.

The allowable range is determined in such a manner that the case where the contact between the HVSW signal line SL1-2 of the ultrasonic probe 1 and the HVSW signal line SL1-1 of the ultrasonic-diagnostic-apparatus main body 3 is defective inside the probe connector 9 and the case where the contact is not defective can be discriminated as voltage values. To be more specific, the allowable range is determined using a reference voltage. The reference voltage is generated by the power supply circuit 17 and is supplied from the power supply circuit 17 to the voltage monitoring circuit 21 through a reference-voltage signal line SL4. As described above, no operating voltage is supplied from the power supply circuit 17 to the HVSW circuit 13 if the contact between the HVSW signal line SL1-2 of the ultrasonic probe 1 and the HVSW signal line SL1-1 of the ultrasonic-diagnostic-apparatus main body 3 is defective inside the probe connector 9. In this case, the input voltage is outside the allowable range; in other words, the input voltage is lower than the reference voltage. Conversely, if the contact is not defective inside the probe connector 9, an operating voltage is supplied from the power supply circuit 17 to the HVSW circuit 13. In this case, the input voltage is within the allowable range; in other words, the input voltage is higher than the reference voltage. The voltage monitoring circuit 21 compares an input voltage with the reference voltage in real time. If the input voltage is higher than the reference voltage, no error signal is generated. If the input voltage is lower than the reference voltage, an error signal is generated. The value of the reference voltage can be determined as an arbitrary value.

In the above, the input voltage and the reference voltage were described as being compared with each other. In order to reduce the load exerted on the voltage monitoring circuit 21, the input voltage and the reference voltage may be divided, and voltages obtained thereby may be compared with each other. The division of the input voltage and the reference voltage is performed, for example, by the voltage monitoring circuit 21.

If a transmission driving signal is supplied to the HVSW circuit 13 in the state where a defective contact occurs in the probe connector 9, there is a fear that the HVSW circuit 13 will be broken down. To prevent the HVSW circuit 13 from breaking down, the voltage monitoring circuit 21 stops supplying the transmission driving signal to the transmitting circuitry 19, upon determination of the occurrence of defective contact. To be specific, if an error signal is generated, the voltage monitoring circuit 21 controls the transmitting circuitry 19 to stop supplying the transmission driving signal to the HVSW circuit 13. Conversely, if no error signal is generated, the voltage monitoring circuit 21 controls the transmitting circuitry 19 to supply the transmission driving signal to the HVSW circuit 13.

If no error signal is supplied, the system control circuitry 15 carries out error processing for the electronic device 25, 27 or 29 to which the monitoring operating voltage is supplied. For example, the system control circuitry 15 is notified, by the notification device 23, of the state where the operating voltage is supplied to the HVSW circuit 13. To be more specific, if an error signal is supplied from the voltage monitoring circuit 21 by way of the system control circuitry 15, the notification device 23 makes a notification that the operating voltage is not supplied to the HVSW circuit 13. For example, a display provided for the ultrasonic-diagnostic-apparatus main body 3 may display a message to the effect that the operating voltage is not supplied to the HVSW circuit 13 in the normal manner. The message is, for example, "DEFECTIVE CONTACT IN THE PROBE CONNECTOR." The notification device 23 may light a lamp provided for the ultrasonic-diagnostic-apparatus main body 3, thereby making a notification that the operating voltage is not supplied to the HVSW circuit 13 in the normal manner. The notification device 23 may generate a voice message "DEFECTIVE CONTACT IN THE PROBE CONNECTOR" or a warning sound through the speaker, thereby making a notification that the operating voltage is not supplied to the HVSW circuit 13 in the normal manner. If an error signal is not supplied from the voltage monitoring circuit 21 through the system control circuitry 15, the monitoring unit 23 makes a notification that the operating voltage is supplied to the HVSW circuit in the normal manner. The notification device 23 may be configured not to make any notification as long as an error signal is not supplied.

In the embodiment described above, the voltage monitoring circuit 21 receives only a voltage from signal line SL2 as an input signal, i.e., the signal line which extends from inside the ultrasonic probe 1 back to the ultrasonic-diagnostic-apparatus main body 3. However, the present embodiment is not limited to this. For example, the voltage monitoring circuit 21 may receive, as an input, not only a voltage from the monitoring voltage signal line SL2 but also a voltage from a signal line (not shown) branching from signal line SL1 inside the ultrasonic-diagnostic-apparatus main body 3. The signal line connects the branch point of the HVSW signal line SL1 inside the ultrasonic-diagnostic-apparatus main body 3 to the voltage monitoring circuit 21. This configuration enables the voltage monitoring circuit 21 to utilize both an input voltage from the ultrasonic probe 1 and an input voltage from the power supply circuit 17. Thereby, the voltage monitoring circuit 21 can check the voltage supply condition very accurately.

In the embodiment described above, the power supply circuit 17 and the voltage monitoring circuit 21 are incorporated in the ultrasonic-diagnostic-apparatus main body 3. However, the present embodiment is not limited to this.

Figure 4:
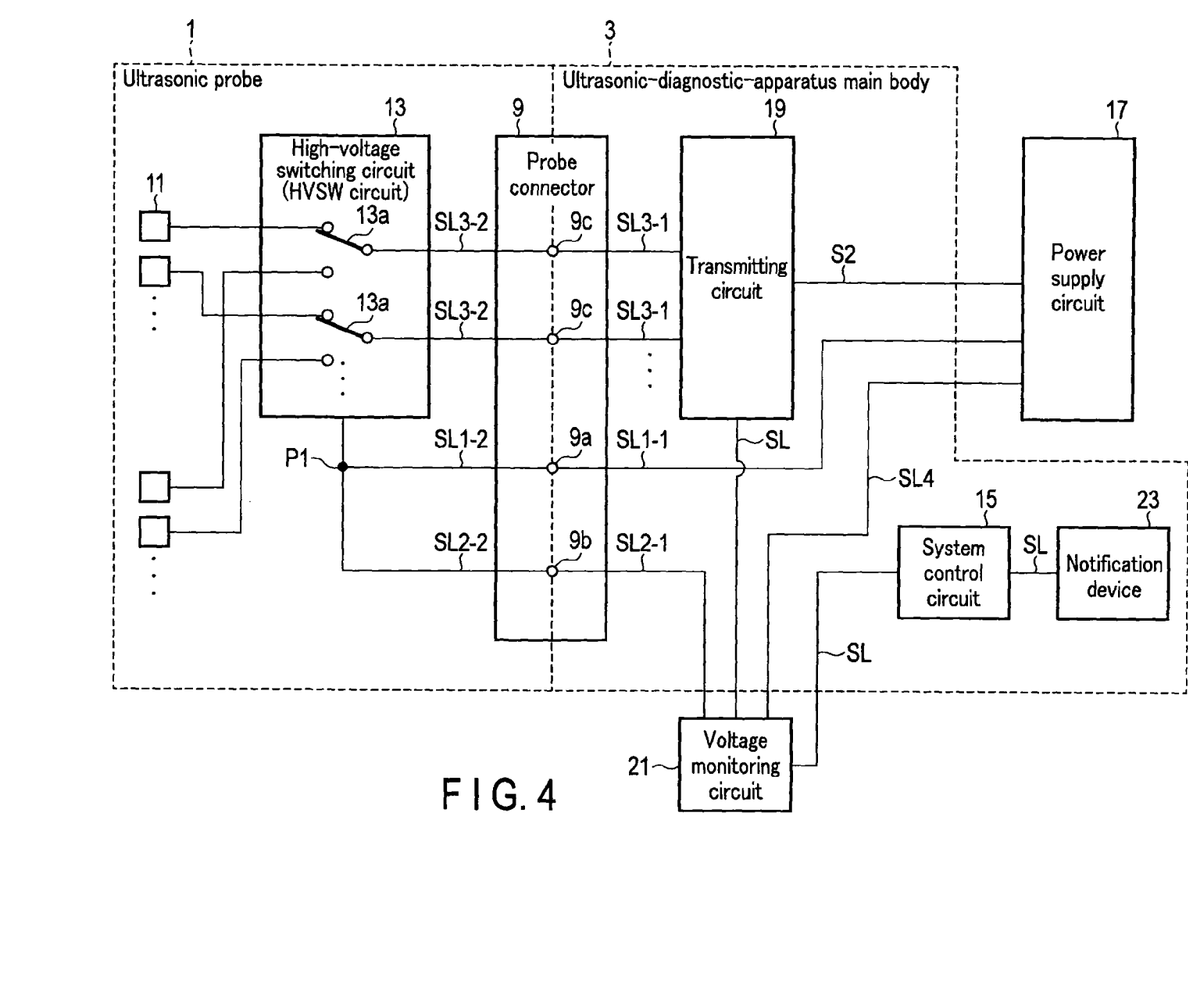
FIG. 4 is a diagram illustrating an ultrasonic probe and an ultrasonic-diagnostic-apparatus main body according to another modification of the first embodiment.

FIG. 4 is a diagram illustrating an ultrasonic probe 1 and an ultrasonic-diagnostic-apparatus main body 3 according to a modification of the first embodiment. As shown in FIG. 4, the power supply circuit 17 may be provided as a circuit external to the ultrasonic-diagnostic-apparatus main body 3. To be more specific, the power supply circuit 17 may be connected directly to the ultrasonic-diagnostic-apparatus main body 3 by use of a connector; alternatively, it may be connected using a cable (not shown). The voltage monitoring circuit 21 is provided as a circuit external to the ultrasonic-diagnostic-apparatus main body 3. To be more specific, the voltage monitoring circuit 21 may be connected directly to the ultrasonic-diagnostic-apparatus main body 3 by use of a connector; alternatively, it may be connected using a cable (not shown). Although the power supply circuit 17 and the voltage monitoring circuit 21 were described as being external to the ultrasonic-diagnostic-apparatus main body 3, either the power supply circuit 17 or the voltage monitoring circuit 21 may be provided as a circuit external to the a circuit external to the ultrasonic-diagnostic-apparatus main body 3. Even where the power supply circuit 17 and the voltage monitoring circuit 21 are external to the ultrasonic-diagnostic-apparatus main body 3, the HVSW circuit 13 may be provided for the probe connector 9.

Second Embodiment

In connection with the first embodiment, the HVSW circuit was described as a device to which an operating voltage is supplied from the power supply circuit. However, the present embodiment is not limited to this, and a device other than the HVSW circuit may be supplied with an operating voltage. The ultrasonic diagnostic apparatus of the second embodiment is featured in that the ultrasonic probe incorporates an electronic device other than the HVSW circuit. The second embodiment will be described. In the description below, structural elements having substantially the same functions will be denoted by the same reference symbols, and a repetitive description will be given only where necessary.

Figure 5:
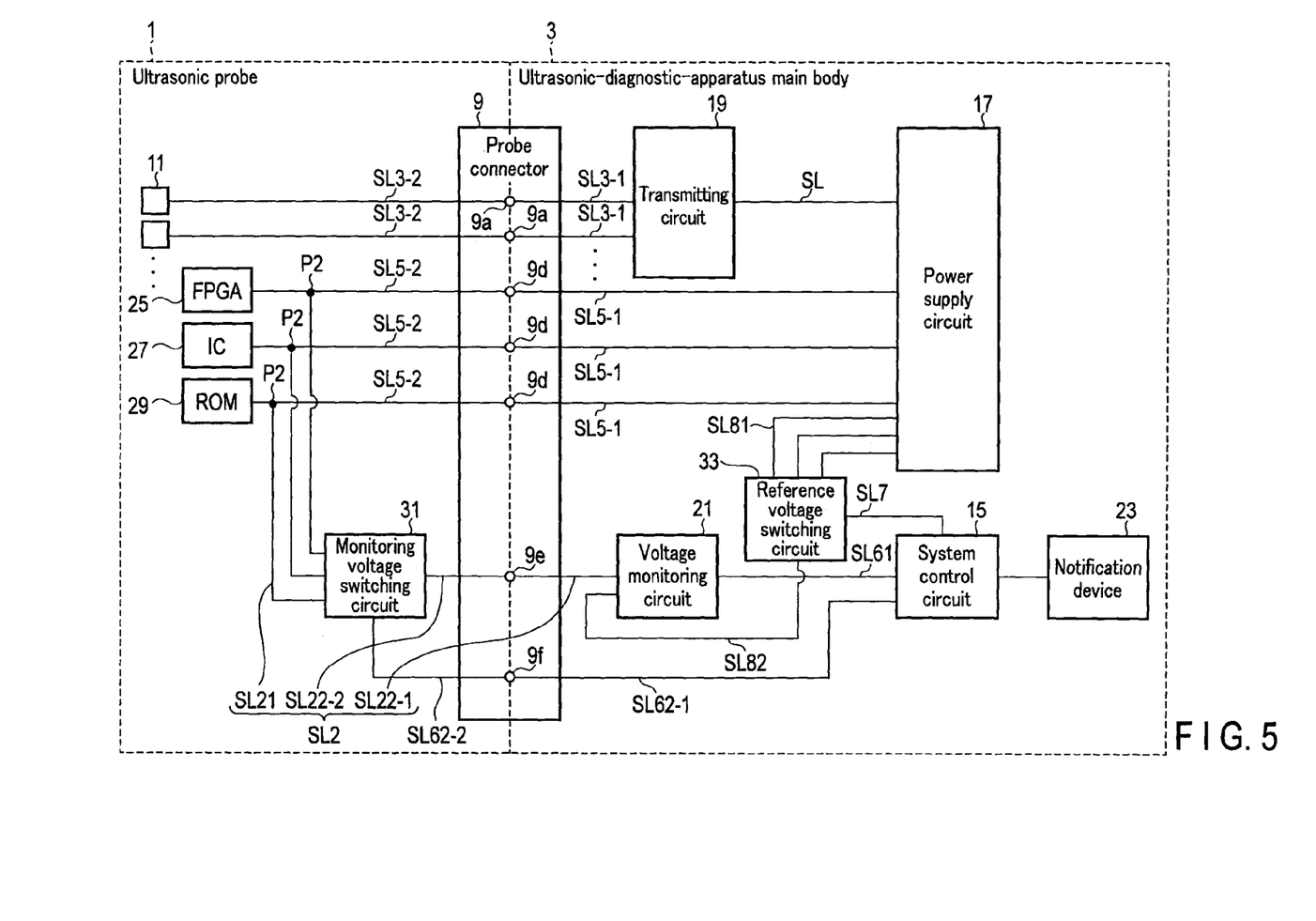
FIG. 5 is a diagram illustrating an ultrasonic probe and an ultrasonic-diagnostic-apparatus main body according to a second embodiment.

FIG. 5 is a diagram illustrating the ultrasonic probe 1 and the ultrasonic-diagnostic-apparatus main body 3 according to the second embodiment. In FIG. 5, a signal receiving circuit and the related system are not illustrated for simplicity.

As shown in FIG. 5, the ultrasonic probe 1 of the second embodiment comprises not only a probe connector 9 and ultrasonic transducers 11 but also electronic devices 25, 27 and 29 and a monitoring voltage switching circuit 31. The electronic devices incorporated in the ultrasonic probe 1 include a field programmable gate array (FPGA) 25, an integrated circuit (IC) 27 and a read only memory (ROM) 29. These electronic devices 25, 27 and 29 are provided for performing signal processing of echo signals and for providing a delay time for a transmission driving signal. The values of the voltages on which the electronic devices operate are different. The electronic devices employed in the second embodiment are not limited to the FPGA, IC and ROM; they may be any types of electronic device that require operating voltages from the power supply circuit 17, such as a central processing unit (CPU) and an application specific integrated circuit (ASIC). The ultrasonic-diagnostic-apparatus main body 3 of the second embodiment comprises a system control circuitry 15 as a central element. It also comprises a reference voltage switching circuit 33, in addition to a power supply circuit 17, a transmitting circuitry 19, a voltage monitoring circuit 21 and a notification device 23.

The second embodiment will be described on the assumption that the HVSW circuit is not provided, for the sake of simplicity. In this case, the transmitting circuitry 19 and the ultrasonic transducers 11 are connected to each other using driving-signal-supply signal lines SL3, the number of which is the same as the number of ultrasonic transducers 11 provided. More specifically, each driving-signal-supply signal line SL3 includes: a first portion SL3-1 which connects the power supply circuit 19 and pin 9a to each other inside the ultrasonic-diagnostic-apparatus main body 3; and a second portion SL3-2 which connects the ultrasonic transducer 11 and pin 9a of the probe connector 9 inside the ultrasonic probe 1.

The ultrasonic probe 1 of the second embodiment is connected to the devices of the ultrasonic-diagnostic-apparatus main body 3 through signal lines SL. Of the signal lines, the signal lines used for connecting the power supply circuit 17 and the electronic devices 25, 27 and 29 are referred to as electronic-device signal lines SL5.

The electronic-device signal lines SL5 connect the power supply circuit 17 and the respective electronic devices 25, 27 and 29 to each other by way of the probe connector 9. More specifically, electronic-device signal lines SL5 include: first portions SL5-1 which connect the power supply circuit 17 and pins 9d of the probe connector 9 to each other inside the ultrasonic-diagnostic-apparatus main body 3; and second portion SL5-2 which connect the respective electronic devices 25, 27 and 29 and pin 9d of the probe connector 9 inside the ultrasonic probe 1.

The monitoring-voltage signal line SL2 employed in the second embodiment includes first monitoring-voltage signal lines SL21 and a second monitoring-voltage signal line SL22. The first monitoring-voltage signal lines SL21 connect the respective electronic devices 25, 27 and 29 to the monitoring voltage switching circuit 31. The first monitoring-voltage signal lines SL21 branch from the respective electronic-device signal lines SL5 and connect the respective electronic devices 25, 27 and 29 to the monitoring voltage switching circuit 31. More specifically, the first monitoring-voltage signal lines SL21 connect the respective branch points P2 on signal lines SL5-2 to the monitoring voltage switching circuit 31. The second monitoring-voltage signal line SL22 connects the monitoring-voltage switching circuit 31 and the voltage monitoring circuit 21 to each other by way of the probe connector 9. More specifically, the second monitoring-voltage signal line SL22 includes: a first portion SL22-2 which connects the monitoring-voltage switching circuit 31 and pin 9e of the probe connector 9 to each other inside the ultrasonic probe 1; and a second portion SL22-1 which connects the voltage monitoring circuit 21 and pin 9e of the probe connector 9 inside the ultrasonic-diagnostic-apparatus main body 3.

The electronic devices 25, 27 and 29 may be incorporated in the probe head 5 of the ultrasonic probe 1 or in the probe connector 9. Where the electronic devices 25, 27 and 29 are incorporated in the probe head 5, branch points P2 are provided in the probe header 5, on the probe cable 7 or in the probe connector 9. Where the electronic devices 25, 27 and 29 are incorporated in the probe connector 9, branch points P2 are provided in the probe connector 9.

The signal line for connecting the voltage monitoring circuit 21 and the system control circuitry 15 to each other by way of the probe connector 9 will be referred to as the first control signal line SL61, and the signal line for connecting the reference voltage switching circuit 33 and the system control circuitry 15 to each other will be referred to as the second control signal line SL62. More specifically, the second control signal line SL6 includes: a first portion SL62-2 which connects the monitoring-voltage switching circuit 31 and pin 9f of the probe connector 9 to each other inside the ultrasonic probe 1; and a second portion SL62-1 which connects the system control circuitry 15 and pin 9f of the probe connector 9 inside the ultrasonic-diagnostic-apparatus main body 3. The signal lines for connecting the power supply circuit 17 and the reference voltage switching circuit 33 to each other will be referred to as the first reference-voltage signal lines SL81, and the signal line for connecting the reference voltage switching circuit 33 and the voltage monitoring circuit 21 will be referred to as the second reference-voltage signal line SL82. Each of the first reference-voltage signal lines SL81 is used for supplying one reference voltage to the reference voltage switching circuit 33.

The power supply circuit 17 generates an operating voltage for operating the transmitting circuitry 19, and further generates different operating voltages for operating the electronic devices 25, 27 and 29 (the latter operating voltages will be referred to as electronic-device operating voltages). The electronic-device operating voltages have different values determined in accordance with the types of electronic devices. Furthermore, the power supply circuit 17 can generate not only the operating voltages but also a plurality of reference voltages to be supplied to the voltage monitoring circuit 21. The reference voltages have different values determined in accordance with the electronic-device operating voltages.

The monitoring-voltage switching circuit 31 selects one voltage to be monitored from among the operating voltages supplied through the first monitoring-voltage signal lines SL21, in accordance with a control signal supplied from the system control circuitry 15 through the probe connector 9. The selected operating voltage to be monitored is supplied to the voltage monitoring circuit 21 through the second monitoring-voltage signal line SL22.

The reference voltage switching circuit 33 selects one reference voltage from among the reference voltages supplied through the first reference-voltage signal lines SL81, in accordance with a control signal supplied from the system control circuitry 15. The reference voltage used for the monitoring operation corresponds to the operating voltage to be monitored, which is selected by the monitoring voltage switching circuit 31. The selected reference voltage used for the monitoring operation is supplied to the voltage monitoring circuit 21 through the second reference-voltage signal line SL82.

The voltage monitoring circuit 21 receives a voltage from the second monitoring-voltage signal line SL22 as an input voltage. To be more specific, the voltage monitoring circuit 21 receives voltages from signal lines SL21 and SL22 as input voltages, i.e., the signal lines branching from signal line SL5 (used for supplying electronic-device operating voltages) and extending from inside the ultrasonic probe 5 back to the ultrasonic-diagnostic-apparatus main body 3. The voltage monitoring circuit 21 monitors voltages applied from the power supply circuit 17 to the electronic devices 25, 27 and 29, utilizing the input voltage from the ultrasonic probe 1. Details of the voltage monitoring circuit 21 will be described later.

Next, a description will be given of an example of the operation performed by the ultrasonic diagnostic apparatus according to the second embodiment. As described above, the voltage monitoring circuit 21 receives only a to-be-monitored operating voltage selected by the monitoring voltage switching circuit 31 as an input voltage. If an existing probe connector 9 is used in the present embodiment, the number of pins it has is limited, and all operating voltages cannot be supplied to the voltage monitoring circuit 21 in terms of the configuration and cost. In addition, if all operating voltages are monitored in parallel, the load applied to the voltage monitoring circuit 21 may be heavy, shortening the life of the voltage monitoring circuit 21. For this reason as well, only an operating voltage to be monitored should be supplied to the voltage monitoring circuit 21.

When the ultrasonic diagnostic apparatus 1 is in operation, the system control circuitry 15 generates a control signal used for selecting an operating voltage to be monitored (the control signal will be hereinafter referred to as an "operating voltage selecting signal"). The operating voltage selecting signal is supplied to the monitor voltage switching circuit 31 through the first control signal line SL5. The operating voltage to be monitored may be selected by the user who operates an operation unit (not shown); alternatively, it may be automatically selected at regular intervals from among a plurality of operating voltages.

Upon receipt of the operating voltage selecting signal, the monitor voltage switching circuit u closes the connection between the first monitor-voltage signal line SL21 corresponding to an operating voltage to be monitored in accordance with a control signal and the second monitor-voltage signal line SL 22, and opens the connection between the other first monitor-voltage signal lines SL21 and the second monitor-voltage signal line SL 22. As a result, only the operating voltage to be monitored passes along the second monitor voltage signal line SL22 and is supplied to the voltage monitoring circuit 21 by way of the probe connector 9.

When the ultrasonic diagnostic apparatus 1 is in operation, the system control circuitry 15 generates a control signal used for selecting a reference voltage corresponding to the operating voltage to be monitored (the control signal will be hereinafter referred to as a "reference voltage selecting signal"). The reference voltage selecting signal is supplied to the reference voltage switching circuit 33 through the second control signal line SL7. The reference voltage used for the monitoring operation is selected unconditionally in accordance with the operating voltage to be monitored.

When the reference voltage selecting signal is supplied, the reference voltage switching circuit 33 closes the connection between the first reference-voltage signal line SL81 corresponding to the operating voltage to be monitored in accordance with a control signal and the second reference-voltage signal line SL 82, and opens the connection between the other first reference-voltage signal lines SL81 and the second reference-voltage signal line SL 82. As a result, only the selected reference voltage used for the monitoring operation is supplied to the voltage monitoring circuit 21 through the second reference-voltage signal line SL82.

To detect a defective contact of each electronic-device signal line SL 5 in the probe connector 9, the voltage monitoring circuit 21 determines whether the input voltage from the second monitoring-voltage signal line SL22 is within an allowable range. The allowable range is determined depending upon an operating voltage to be monitored, i.e., the type of electronic device 25, 27 or 29. Each allowable range is determined in accordance with a reference voltage corresponding to the operating voltage.

As in the first embodiment, the voltage monitoring circuit 21 compares an input voltage selected by the monitoring voltage switching circuit 31 (i.e., an operating voltage to be monitored) with the reference voltage selected by the reference voltage switching circuit 33 in real time. If the input voltage is lower than the reference voltage, an error signal is generated. If the input voltage is higher than the reference voltage, an error signal is not generated. The value of the reference voltage can be determined by the user as an arbitrary value. The error signal is supplied to the system control circuitry 15.

If the error signal is supplied, the system control circuitry 15 carries out error processing for the electronic device 25, 27 or 29 to which the monitoring operating voltage is supplied. For example, the system control circuitry 15 controls the notification device 23 to make a notification that the power supply circuit 17 and the electronic devices 25, 27 and 29 are not in good contact in the probe connector 9, as in the first embodiment. To be more specific, if an error signal is supplied from the voltage monitoring circuit 21 by way of the system control circuitry 15, the notification device 23 makes a notification that the operating voltage is not supplied to the HVSW circuit 29. If no error signal is supplied from the voltage monitoring circuit 21 by way of the system control circuitry 15, the notification device 23 makes a notification that the operating voltages are supplied to the electronic devices 25, 27 and 29 in the normal manner.

In the second embodiment described above, the power supply circuit 17 and the voltage monitoring circuit 21 are incorporated in the ultrasonic-diagnostic-apparatus main body 3. However, the present embodiment is not limited to this. As in the first embodiment, the power supply circuit 17 and the voltage monitoring circuit 21 may be provided as circuits external to the ultrasonic-diagnostic-apparatus main body 3.

As described above, the ultrasonic diagnostic apparatus of the second embodiment comprises an ultrasonic probe 1, and an ultrasonic-diagnostic-apparatus main body 3 which is detachably connected to the ultrasonic probe 1 through the probe connector 9. The power supply circuit 17 is incorporated in the ultrasonic-diagnostic-apparatus main body 3 and generates operating voltages for operating various devices 13, 25, 27 and 29 of the ultrasonic probe 1. Signal lines SL1 and SL4 connect the power supply circuit 17 to the devices 13, 25, 27 and 29 by way of the probe connector 9, so as to supply operating voltages from the power supply circuit 17 to the devices 13, 25, 27 and 29. The voltage monitoring circuit 21 is incorporated in the ultrasonic-diagnostic-apparatus main body 3 and monitors voltages supplied to the electronic devices 13, 25, 27 and 29, utilizing the input voltage from the ultrasonic probe 1. To supply input voltages to the voltage monitoring circuit 21, signal line SL2 branches from signal lines SL1 and SL4 inside the ultrasonic probe 1 and connects the devices 13, 25, 27 and 29 and the voltage monitoring circuit 21 to each other by way of the probe connector 9.

With the configuration described above, the voltage monitoring circuit 21 of the ultrasonic diagnostic apparatus of the embodiment monitors a voltage from signal line SL2, i.e., the signal line which extends from inside the ultrasonic probe 1 back to the ultrasonic-diagnostic-apparatus main body 3. The ultrasonic diagnostic apparatus of the present embodiment differs from the ultrasonic probe described in Patent Document 1 in that the voltage monitoring circuit 21 is provided inside the ultrasonic-diagnostic-apparatus main body 3. With this structure, the ultrasonic diagnostic apparatus of the embodiment can monitor the operating voltages supplied to the devices 13, 25, 27 and 29 at low cost even if signal lines SL1 and SL5 (used for supplying the operating voltages to the devices 13, 25, 27 and 29) are not in good contact inside the probe connector 9. Even where the operating voltages of a plurality of devices 13, 25, 27 and 29 are supplied from the ultrasonic-diagnostic-apparatus main body 3 to the ultrasonic probe 1, the number of pins which the probe connector 9 additionally requires is two.

According to the present embodiment, the operating voltages of the devices provided in the ultrasonic probes can be accurately monitored at low cost.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus comprising (i) an ultrasonic probe including a head, a cable and a connector; and (ii) an ultrasonic-diagnostic-apparatus main body connected to the ultrasonic probe through the connector, said ultrasonic diagnostic apparatus comprising:
    an electric circuit provided in the ultrasonic probe;
    a first signal line passing through the cable and connected at one end to the electric circuit and at another end to the connector;
    a power supply circuit provided in the main body and configured to generate an operating voltage of the electric circuit;
    a second signal line provided inside the main body and connected at one end to the power supply circuit, the second signal line being connected at another end to the first signal line when the main body is connected to the ultrasonic probe;
    a third signal line connected at one end to the first signal line and at another end to the connector;
    a voltage monitoring circuit provided in the main body and configured to monitor a voltage supplied to the electric circuit, utilizing an input voltage; and
    a fourth signal line provided inside the main body and connected at one end to the voltage monitoring circuit, the fourth signal line being connected at another end to the third signal line when the main body is connected to the ultrasonic probe.

2. The ultrasonic diagnostic apparatus according to claim 1, wherein
    the ultrasonic probe further includes a plurality of ultrasonic transducers which transmit and receive ultrasonic waves,
    the main body comprises a transmitting circuitry configured to generate a driving signal for driving the ultrasonic transducers, and
    the electric circuit is an ultrasonic transducer switching circuit which switches connections between the ultrasonic transducers and the transmitting circuitry.

3. The ultrasonic diagnostic apparatus according to claim 1, wherein
    the ultrasonic probe comprises a monitoring voltage switching circuit,
    the electric circuit includes a plurality of electronic circuits,
    the power supply circuit is configured to generate a plurality of operating voltages for the electronic circuits, and
    the monitoring voltage switching circuit switches connections between the electronic circuits and the voltage monitoring circuit such that an operating voltage to be monitored, one of the operating voltages, is supplied to the voltage monitoring circuit.

4. The ultrasonic diagnostic apparatus according to claim 3, wherein
    the main body further comprises a reference voltage switching circuit and a reference-voltage signal line,
    the power supply circuit is configured to generate a plurality of reference voltages corresponding to the operating voltages,
    the reference-voltage signal line comprises a first reference-voltage signal line connecting the reference voltage switching circuit to the voltage monitoring circuit to each other, and a plurality of second reference-voltage signal lines connecting the power supply circuit and the reference voltage switching circuit to each other and used for respective ones of the reference voltages,
    the reference voltage switching circuit switches connections between the second reference-voltage signal lines and the first reference-voltage signal line such that a reference voltage to be monitored, which is one of the reference voltages and corresponds to the operating voltage to be monitored, is supplied to the voltage monitoring circuit.

5. The ultrasonic diagnostic apparatus according to claim 1, wherein
    the main body further comprises a notification device,
    the voltage monitoring circuit determines a voltage supply to the electric circuit based on comparison between the input voltage and a reference voltage supplied from the power supply circuit, and
    the notification device makes a notification regarding the voltage supply.

6. The ultrasonic diagnostic apparatus according to claim 1, wherein
    the ultrasonic probe further includes a plurality of ultrasonic transducers which transmit and receive ultrasonic waves,
    the main body comprises a transmitting circuitry configured to generate a driving signal for driving the ultrasonic transducers, and
    the voltage monitoring circuit determines whether or not the input voltage is within an allowable range, and stops the transmitting circuitry if the input voltage is determined to be outside the allowable range.

7. The ultrasonic diagnostic apparatus according to claim 1, wherein the first signal line and the third signal line are connected to each other at a point located inside the head.

8. The ultrasonic diagnostic apparatus according to claim 1, wherein the first signal line and the third signal line are connected to each other at a point located inside the cable.

9. The ultrasonic diagnostic apparatus according to claim 1, wherein the first signal line and the third signal line are connected to each other at a point located inside the connector.

10. The ultrasonic diagnostic apparatus according to claim 1, wherein the electric circuit is provided in one of the head and the connector.

* * * * *